United States Patent [19]

de Vries

[11] 4,116,873

[45] Sep. 26, 1978

[54] LUBRICATING OIL COMPOSITION CONTAINING GROUP I OR GROUP II METAL OR LEAD SULFONATES

[75] Inventor: Louis de Vries, Greenbrae, Calif.

[73] Assignee: Chevron Research Company, San Francisco, Calif.

[21] Appl. No.: 682,073

[22] Filed: May 10, 1976

Related U.S. Application Data

[63] Continuation-in-part of Ser. No. 585,411, Jun. 9, 1975, abandoned.

[51] Int. Cl.$^2$ .................. C10M 1/40; C10M 3/34; C10M 5/22; C10M 7/38
[52] U.S. Cl. .................. 252/33; 260/435 R; 260/513 R
[58] Field of Search .......... 252/33; 260/513 R, 435 R

[56] References Cited

U.S. PATENT DOCUMENTS

| | | | |
|---|---|---|---|
| 2,865,957 | 12/1958 | Logan | 252/33 |
| 3,219,580 | 11/1965 | Stratton | 252/33 |
| 3,827,979 | 8/1974 | Piotrowski et al. | 252/33 |
| 3,959,164 | 5/1976 | Sabol | 252/33 |

*Primary Examiner*—Irving Vaughn
*Attorney, Agent, or Firm*—C. J. Tonkin; L. L. Vaughan

[57] ABSTRACT

Oil-soluble detergent-dispersant Group I and Group II metal or lead salts of substantially saturated hydrocarbyl-substituted ethylsulfonic acids, processes for preparing these salts, lubricating oil additive concentrates and lubricating oil compositions containing them are disclosed.

35 Claims, No Drawings

LUBRICATING OIL COMPOSITION CONTAINING GROUP I OR GROUP II METAL OR LEAD SULFONATES

CROSS REFERENCE TO RELATED APPLICATIONS

This application is a continuation-in-part of U.S. application Ser. No. 585,411, filed June 9, 1975, now abandoned.

BACKGROUND OF THE INVENTION

1. Field of the Invention

This invention relates to new lubricating oil additives, processes for preparing them, and lubricating oil additive concentrates and lubricating oil compositions containing these additives. More particularly, this invention relates to oil-soluble Group I or Group II metal or lead hydrocarbyl ethylsulfonates.

Lubricating oil compositions, particularly for use in internal combustion engines, perform many functions besides simply lubricating relatively moving parts. Modern, highly compounded lubricating oil compositions provide anti-wear, anti-oxidant, extreme-pressure and anti-rust protection and maintain the cleanliness of the engine.

2. Description of the Prior Art

Mixon et al, U.S. Pat. No. 2,367,468, teach reacting an olefin polymer, preferably having a molecular weight of 500 to 3000, with chlorosulfonic acid and then forming the metal salt.

Knowles et al, U.S. Pat. No. 2,683,161, teach stabilization by the heating to 110° to 300° C of arylalkane sulfonates of the formula $R_1-(SO_2-O-R_2)x$. The sulfonates are prepared from a saturated aliphatic hydrocarbon which has been reacted with: (1) chlorine and sulfur dioxide; and (2) a phenol. $R_1$ is an aliphatic radical derived from a petroleum hydrocarbon containing saturated branched-chain hydrocarbons, preferably of from 6 to 24 carbon atoms. These compounds are proposed for use as plasticizers and functional fluids.

Distler, U.S. Pat. No. 3,133,948, teaches preparing vinylsulfonates of aromatic hydroxy compounds by reacting carbyl sulfate with an aromatic hydroxy compound in an aqueous alkaline medium at a pH between 7.5 and 11.5 to yield an aryl vinylsulfonate. Suitable aromatic hydroxy compounds include ortho- and para-chlorophenol. Carbyl sulfate is prepared from the reaction of ethylene with sulfur trioxide or oleum.

Klass et al, U.S. Pat. No. 3,158,639, state that carbyl sulfate has been known since 1836 and teach that it may be prepared by reacting ethylene with sulfur trioxide at a 1:2 mol ratio either in solution or in the vapor phase, usually at room temperature or lower to avoid charring.

Friedrichsen and Distler, U.S. Pat. No. 3,205,249, disclose aryl esters of unsaturated sulfonic acids prepared by reacting an olefin containing at least 1 methyl and/or methylene group adjacent to the double bond linkage with an aryl vinylsulfonate at temperatures between 100°-300° C. Suitable olefins contain between 3 and 20 carbon atoms. These compounds are proposed for use as plasticizers and textile auxiliaries.

British Pat. No. 1,246,545 teaches a sulfonated olefin prepared by halogenating an olefin, dehydrohalogenating to a conjugated diene, sulfonating by conventional methods and, optionally, neutralizing with an alkaline earth metal.

SUMMARY OF THE INVENTION

This invention comprises oil-soluble Group I and Group II metal and lead salts of substantially saturated aliphatic hydrocarbylethylsulfonic acids in which the substantially saturated hydrocarbyl substituent contain at least 25 carbon atoms. These salts have excellent detergency and dispersancy properties in lubricating oils.

They can be prepared by reacting the aryl ester of a substantially saturated hydrocarbyl ethylsulfonic acid with from about 1 to 30 equivalents per equivalent of said ester of a Group I or Group II metal oxide or hydroxide.

The oil-soluble sulfonates of this invention can also be prepared by first preparing a neutral Group I metal salt of the sulfonate and then converting this material by metathesis into the Group II metal or lead sulfonate.

Included with this invention are the neutral metal salts (as described above) overbased with a Group I metal carbonate and a method for the preparation of these salts.

Lubricating oil additive concentrates comprise 85% to 15% weight of an oil of lubricating viscosity and 15% to 85% wieght of an oil-soluble Group I or Group II metal or lead sulfonate described above. Lubricating oil compositions comprise (1) a major amount of an oil of lubricating viscosity, and (b) a minor amount effective to provide detergency of the oil-soluble Group I or Group II metal or lead sulfonate described above.

The predominant organic group believed to be formed from the sulfonate ester group and the basically reacting Group I and Group II metal and lead compounds is a metal sulfonate. Throughout this discussion the reaction products obtained as described above will be generically described as metal sulfonates.

The metal sulfonates of this invention are lubricating oil additives having excellent detergent and dispersant properties. They also aid in preventing varnish. They are prepared from sulfonate esters which are obtained from materials synthesized from readily available, inexpensive raw materials.

DETAILED DESCRIPTION OF THE INVENTION

The oil-soluble Group I and Group II metal or lead salts of substantially saturated aliphatic hydrocarby ethylsulfonic acids, the substantially saturated hydrocarbyl substituent containing at least 25 aliphatic carbon atoms, of this invention are prepared by reacting an aryl ester of the formula described below with a Group I or Group II metal oxide or hydroxide:

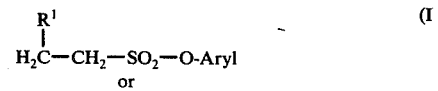

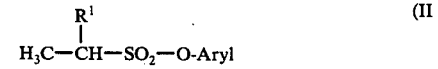

where $R^1$ is a substantially saturated aliphatic hydrocarbyl substituent containing enough carbon atoms to make the sulfonate oil soluble.

Generally $R^1$ will contain about 25 to about 350 carbon atoms, preferably from about 25 to about 300 carbon atoms, and more preferably from about 50 to about 200 carbon atoms.

The hydrocarbyl substituent is substantially saturated. By "substantially saturated" is meant that at least about 95% of the total number of carbon-to-carbon covalent linkages are saturated linkages. An excessive proportion of unsaturated linkages makes the molecules susceptible to oxidation, degradation, and polymerization. This makes the products unsuitable for many uses in hydrocarbon oils.

The substantially saturated hydrocarbyl substituent may contain polar substituents as long as they are present in such minor proportions that they do not significantly alter the hydrocarbon character of the hydrocarbyl group. Such polar substituents are exemplified by chloro, keto and alkoxy. It is preferred that these groups not be present. The upper limit on these polar substituents in the hydrocarbyl group is about 10% by weight.

The substantially saturated hydrocarbyl substituent is derived primarily from high-molecular-weight, substantially saturated petroleum fractions and substantially saturated olefin polymers, particularly polymers of monoolefins having from 2 to about 30 carbon atoms. Especially useful polymers are the polymers of 1-monoolefins such as ethylene, propene, 1-butene, isobutene, 1-hexene, 1-octene, 2-methyl-1-heptene, 3-cyclohexyl-1-butene, and 2-methyl-5-propyl-1-hexene. Polymers of medial olefins, i.e., olefins in which the olefinic linkage is not at the terminal position, are also useful. Such olefins are illustrated by 2-butene, 3-pentene, and 4-octene.

Also useful are interpolymers of olefins such as those illustrated above with other interpolymerizable olefinic substances such as other 1-olefins, aromatic olefins, cyclic olefins, and polyolefins. Such interpolymers include, for example, those prepared by polymerizing isobutene with styrene, isobutene with butadiene, propene with isoprene, ethylene with piperylene, ethylene with propene, isobutene with chloroprene, isobutene with p-methyl styrene, 1-hexene with 1,3-hexadiene, 1-octene with 1-hexene, 1-heptene with 1-pentene, 3-methyl-1-butene with 1-octene, 3,3-dimethyl-1-pentene with 1-hexene, and isobutene with styrene and piperylene.

The relative proportions of the monoolefins to the other monomers in the interpolymers influence the stability and oil solubility of the final compositions. To promote oil solubility and stability, the interpolymers should be substantially aliphatic and substantially saturated, i.e., they should contain at least about 80%, preferably about 95%, on a weight basis, of units derived from the aliphatic monoolefins and no more than about 5% of olefin linkages based on the total number of carbon-to-carbon covalent linkages. In most instances there will be about one olefinic linkage per molecule. The percentage of olefinic linkages is preferably less than about 2% of the total number of carbon-to-carbon covalent linkages.

Specific examples of such interpolymers include copolymers of 95% (by weight) of isobutene with 5% styrene, terpolymer of 98% of isobutene with 1% of piperylene and 1% of chloroprene, terpolymer of 95% of isobutene with 2% of 1-butene and 3% of 1-hexene, terpolymer of 60% of isobutene with 20% of 1-pentene and 20% of 1-octene, copolymer of 80% 1-hexene and 20% of 1-heptene, terpolymer of 90% of isobutene with 2% of cyclohexene and 8% of propene, and copolymer of 80% of ethylene and 20% of propene.

The aryl sulfonates of formulas I and II are prepared by adducting an aryl vinylsulfonate to a hydrocarbon from the sources mentioned above. This adduction is carried out using conventional techniques such as those used to adduct maleic anhydride to hydrocarbon substituents in preparing hydrocarbyl succinic anhydrides. The aryl substituent is not displaced during the adduction reaction.

In one adduction method, the hydrocarbyl substituent source is charged to the reaction vessel and heated with stirring. The aryl vinylsulfonate is added to the reaction vessel and the reaction mass is heated to the reaction temperature, generally about 100°–300° C, preferably 150°–250° C. Usually the reaction is completed in about 1 to about 48 hours, or preferably from about 2 to about 24 hours at the preferred reaction temperatures. The reactivity of the hydrocarbyl substituent source in the adduction reaction can often be enhanced if it is first chlorinated. For example, an excellent hydrocarbyl substituent source is polyisobutene. In the adduction reaction, polyisobutenyl chloride reacts faster and at lower temperatures.

The adduct can be purified by conventional methods. For example, the lower boiling impurities, such as excess phenylvinylsulfonate, are removed by distillation or codistillation with a hydrocarbon solvent of intermediate boiling range. A typical solvent is a solvent-refined neutral oil. The distillation process is usually carried out at a reduced pressure. The adduct is further purified by diluting it with an aliphatic hydrocarbon solvent and filtering to remove any resinous by-products or polymeric material. Finally, the solvent is removed by stripping to yield the pure product.

In formulas I and II, "aryl" is an aryl radical or a substituted aryl radical. The aryl radical is derived from an aromatic hydroxy compound which can react with carbyl sulfate to form an aryl vinylsulfonate. The aryl vinylsulfonate is converted to the compounds of formulas I and II as described above.

Suitable aromatic hydroxy compounds contain at least one carbocyclic aromatic ring and at least one hydroxy group attached directly to the carbocyclic aromatic ring. The aromatic ring may be substituted with mild electron withdrawing groups which promote its reactivity with the carbyl sulfate. Preferred electron withdrawing groups are halo, especially chloro and bromo. A particularly useful group is a single chloro group located either ortho or para to the hydroxy group. The aromatic ring may also be substituted with mild electron-donating groups such as methyl and ethyl.

Preferred aromatic hydroxy compounds contain 1 to 3 carbocyclic aromatic rings and 1 to 3 hydroxy groups. If the aromatic hydroxy compound contains more than 1 aromatic ring, the rings may be condensed (as in naphthol), linked by single bond (as in diphenol) or linked via a short-chain bridge (as in diphenolmethane).

The most preferred aromatic compounds are those of the formula:

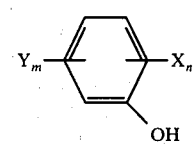

wherein X is halo, Y is $C_1-C_6$ alkyl, $n$ is zero or 1-2, and $m$ is zero, 1 or 2.

Suitable aromatic hydroxy compounds include phenol, the cresols, the xylenols, p-tertiary butylphenol, nonylphenol, dodecylphenols, o-chlorophenol, p-chlorophenol, 4-chloro-2-methylphenol, ortho- and meta-methyl-4,4'-dihydroxydiphenyl, 4,4'-dihydroxydiphenylmethane, 2,2-bis-(4'-hydroxyphenyl)propane, bis-(4'-hydroxyphenyl)sulfone, resorcinol, 3-cyanophenol, 4,4'-dihydroxydiphenyl sulfoxide, 3-iodophenol, octadecylphenols, 4-cyclohexylphenol, 4-cyclododecylphenol, 4-dibutylaminophenol, 4-(N-methyl-N-ethyl)aminophenol, 3-methoxyphenol and 4-butoxyphenol.

The aryl ester of vinylsulfonic acid can be prepared by several available techniques. U.S. Pat. No. 3,121,730 teaches reacting a beta-chloroethanesulfonyl chloride with phenol in an aqueous medium at a pH of between 7.5 and 11.5. The reaction proceeds with a loss of 2 mols of hydrogen chloride to yield phenyl vinylsulfonate. U.S. Pat. No. 3,133,948 teaches reacting carbyl sulfate with an aromatic hydroxy compound in an aqueous alkaline medium at a pH between 7.5 and 11.5 to yield a aryl vinylsulfonate.

Another more convenient method does not allow the carbyl sulfate to solidify after it is prepared because carbyl sulfate is difficult to use after it has solidified. In this method the carbyl sulfate is prepared by reacting ethylene with sulfur trioxide at temperatures above the melting point of carbyl sulfate, about 110°-180° C, preferably about 150°-160° C. The molten carbyl sulfate is immediately introduced into an aqueous caustic solution of the aromatic hydroxy compound. The carbyl sulfate reacts with the aromatic hydroxy compound to yield the aryl ester of vinylsulfonic acid plus sodium sulfate. Preferably the aqueous solution is maintained between 0° C and 25° C and at a pH of 9 to 11. After the sulfonate ester is isolated from the aqueous solution, it can be converted to the adduct as described above.

The carbyl sulfate and the aromatic hydroxy compound are usually reacted in equivalent quantities, i.e., a molar ratio of about 1:1 phenol/carbyl sulfate molar ratio for monohydric phenols and about a 1:2 phenol/carbyl sulfate molar ratio for dihydric phenols. Since the carbyl sulfate tends to hydrolyze in an aqueous solution, an excess must be added in order to obtain 1:1 equivalent ratio with the aromatic hydroxy compound.

The Metal Salts

The metal sulfonates are prepared using any Group I and Group II metals or lead compound which forms a salt with the sulfonic acid moiety and which yields a salt useful as a detergent in lubricating oil compositions. Preferably, the Group I metal compounds are lithium, sodium and potassium compounds and the Group II metal compounds are magnesium, calcium, strontium, barium and zinc. The lead compound must be in the +2 valence state, i.e., Pb++. More preferably, the Group I metal compounds are sodium and potassium compounds and the Group II metal compounds are magnesium, calcium and barium compounds.

The Group I and Group II metal salt of this invention can be prepared by a variety of means. One method is combining the metal hydroxide or oxide with the aryl ester of the hydrocarbyl ethylsulfonic acid described above. This is generally carried out in the presence of a hydroxylic promoter such as 1,3-propanediol, 1,4-butanediol, diethylene glycol, butyl cellosolve, propylene glycol, 1,4-butyleneglycol, methyl carbitol, ethanolamine, diethanolamine, N-methyl-diethanolamine, dimethyl formamide, N-methyl acetamide, dimethyl acetamide, and especially water, methanol or ethylene glycol. An inert solvent is usually used and the reaction mixture is heated. The metal oxide or hydroxide hydrolyzes the ester group to yield the metal sulfonate. Thereafter, the promoter, solvent and by-products can be removed to yield the metal sulfonate.

Under certain circumstances, it may be more convenient to prepare a Group I metal salt of the sulfonate and convert this material by metathesis into the Group II metal or lead sulfonate. In this method the aryl hydrocarbyl ethylsulfonate is reacted with a Group I metal hydroxide, such as sodium or potassium hydroxide. The sodium or potassium sulfonate obtained can be partially purified by aqueous extraction. Thereafter, the Group I metal sulfonate is reacted with a Group II metal salt or a lead salt to form the Group II metal or lead sulfonate. A suitable Group II metal salt is a halide, particularly a chloride because of its low cost. A suitable lead compound is lead nitrate or lead acetate. Typically, the sodium or potassium sulfonate is combined with an aqueous chloride solution of the Group II metal or lead salt and stirred for sufficient time to allow metathesis to occur. The water phase is then removed and the solvent may be evaporated if desired.

If a salt having a completely saturated hydrocarbyl group is desired, it is necessary to hydrogenate the Group I or Group II metal or lead sulfonate with hydrogen, using, for example, a conventional noble metal or noble metal oxide hydrogenation catalyst, such as platinum or platinum oxide.

The sulfonates can be overbased. Overbased materials are characterized by a metal content in excess of that which would be present according to the stoichiometry of the metal cation and the particular organic compound said to be overbased. Thus an oil-soluble monosulfonic acid neutralized with a Group II oxide or hydroxide, e.g., calcium oxide or hydroxide, produces a normal sulfonate containing one equivalent of calcium for each equivalent of acid. In other words, the normal metal sulfonate will contain one mol of calcium for each two mols of the monosulfonic acid.

By applying well-known procedures, "overbased" or "basic" complexes of the sulfonic acids can be obtained. These overbased materials can contain metal many times in excess of that required to neutralize the acid. These stoichiometric excesses can vary considerably, e.g., from about 0.1 to about 30 or more equivalents depending upon the reactants, the process conditions, etc.

The degree of overbasing can be expressed by several ways. One method is to describe the "metal ratio". This method describes the ratio of the total chemical equivalents of metal in the product to the chemical equivalents of the compound said to be overbased, based on the known chemical reactivity and stoichiometry of the two reactants. Thus in a normal (neutral) calcium sulfonate, the metal ratio is 1 and in overbased sulfonate the metal ratio can range from about 1.1 to 30 or more, generally from about 5 to 20.

Another method of expressing the degree of overbasing is to describe the "base ratio". This method describes the ratio of chemical equivalents of basic metal to the chemical equivalents of neutral metal. The neutral metal is the metal which would be expected to react with the compound to be overbased, i.e., the metal required to neutralize the sulfonic acid. The basic metal is the metal in excess of the neutral metal, i.e., it is the metal available to neutralize acidic combustion products. Thus a normal (neutral) calcium sulfonate has a base ratio of 0 and an overbased sulfonate can have a base ratio ranging from about 0.1 to about 30 or more, generally about 4 to about 19.

Another method of specifying the degree of overbasing of dispersants such as the sulfonates is by stating the alkalinity value (AV) of the composition. The method for determining the alkalinity value of an overbased composition is set forth in ASTM Method D-2896. Briefly, the alkalinity value is stated as the number of milligrams of potassium hydroxide per gram of composition to which the overbasing is equal. For example, if the composition is overbased to the extent that it has the same acid neutralizing capacity per gram as 10 milligrams of potassium hydroxide, the composition is given an alkalinity value of 10. The lower limit of alkalinity value is zero for a neutral sulfonate, with values of 10 to 50 being common for slightly overbased sulfonates. Highly overbased sulfonates have values ranging from about 275 to about 400.

A discussion of the general method of preparing overbased sulfonates and other overbased products is disclosed in U.S. Pat. No. 3,496,105.

Lubricating Oil Concentrates

Lubricating oil additive concentrates contain from about 85% to about 15% weight of an oil of lubricating viscosity and from about 15% to about 85% weight of the oil-soluble Group I and Group II metal and/or lead sulfonates of this invention. The concentrates contain as much of the oil-soluble sulfonate as is practical, since the concentrates are prepared to reduce shipping costs, storage requirements, etc. Typically, the concentrates contain only sufficient diluent to make them easy to handle during shipping and blending. Any inert diluent is suitable, preferably an oil of lubricating viscosity is used so that the concentrate may be readily mixed with lubricating oils to prepare lubricating oil compositions. Suitable lubricating oils typically have viscosities in the range of from about 35 to about 1000 Saybolt Universal Seconds (SUS) at 38° C (100° F), although any oil of lubricating viscosity can be used.

Lubricating Oil Compositions

Lubricating oil compositions comprise (a) an oil of lubricating viscosity, usually in a major amount, and (b) an amount effective to provide detergency (usually a minor amount) of at least one of the oil-soluble Group I and Group II metal and lead sulfonates of this invention.

Suitable lubricating oils are oils of lubricating viscosity derived from petroleum or synthetic sources. The oils can be paraffinic, naphthenic, halo-substituted hydrocarbons, synthetic esters, or combinations thereof. Oils of lubricating viscosity have viscosities in the range of 35 to 50,000 Saybolt Universal Seconds (SUS) at 38° C (100° F), and more usually from about 50 to 10,000 SUS at 38° C (100° F). The amount of the oil-soluble Group I and/or Group II metal and/or lead sulfonate which is incorporated in the lubricating oil composition to provide the amount necessary for detergency varies widely with the particular sulfonate used as well as the use to which the lubricating oil composition is put.

In general, the lubricating compositions will contain from about 0.1% to about 15% by weight of the oil-soluble metal sulfonate. More usually, the lubricating oil composition of the invention will contain from about 0.5% to about 10% weight of the metal sulfonate and more usually from about 1% to about 8% weight of the metal sulfonate.

The overbased metal sulfonates of this invention can be incorporated in lubricating oils to obtain an alkalinity value of from about 0.1 to about 100, more commonly of from about 2 to about 75, in order to control extreme corrosive wear.

These lubricating oil compositions are useful for lubricating internal combustion engines. The lubricating oils not only lubricate the engine but, because of their detergency properties, help maintain a high degree of cleanliness of the lubricated parts.

Other conventional additives which can be used in combination with the metal sulfonates of this invention include ashless dispersants such as the type disclosed in U.S. Pat. No. 3,172,892, 3,219,666 and 3,381,022; neutral and basic calcium and barium petroleum sulfonates, corrosion inhibitors, oxidation inhibitors, antifoam agents, viscosity index improvers, and pour point depressants. Typical additives include chlorinated wax, benzyldisulfide, sulfurized sperm oil, sulfurized terpene, phosphorus esters, such as trihydrocarbon phosphites, metal dithiocarbamates, such as zinc dioctyldithiocarbamate, metal phosphorodithioates, such as zinc dioctylphosphorodithioate, polyisobutylene having an average molecular weight of 100,000, etc.

EXAMPLES

The following examples are included to further illustrate the invention.

EXAMPLE 1A — PREPARATION OF O-CHLOROPHENYL VINYLSULFONATE

A 5-liter flask (the o-chlorophenyl vinylsulfonate reactor) is charged with 1280 ml of water, 640 ml of 1,2-dichloroethane, 150 ml of 25% sodium hydroxide in water, and 350 gm (2.72 mols) of o-chlorophenol. This mixture is stirred and cooled to 0° C in a dry ice-acetone bath. A dropping funnel is charged with 908 q of commercial sulfur trioxide (typically contains 850–860 g of liquid sulfur trioxide). Ethylene is intoduced to a 500 ml flask (the carbyl sulfate reactor). After the ethylene flow is established, sulfur trioxide is introduced into this reaction vessel from its dropping funnel. A slight excess of ethylene is used. The reaction between ethylene and sulfur trioxide takes place rapidly with evolution of heat to yield carbyl sulfate. The reaction vessel warms to approximately 150°–170° C. At these temperatures, the liquid carbyl sulfate, which has a melting point of about 109°–110° C, drips into the stirred cold sodium chlorophenate solution in the 5-liter flask.

The carbyl sulfate and sodium chlorophenate react under alkaline conditions (pH 9–11) to yield o-chlorophenyl vinylsulfonate and sodium sulfate.

After all the sulfur trioxide has been added, the reaction mixture is stirred for about 30 minutes and then neutralized with concentrated HCl to pH 5. The mixture is then heated to 40° C, the organic layer is removed, filtered through Celite filter aid and stripped to an end point of 100° C at 2 to 5 mm Hg.

Typical crude yields of o-chlorophenyl vinylsulfonate from a 350 g charge of o-chlorophenol vary from 550 to 615 grams. Typically, the crude product contains less than 1% unreacted o-chlorophenol, and has 15.3%–16.4% sulfur, 15.0%–15.6% chlorine.

EXAMPLE 1B — PREPARATION OF PHENYL VINYLSULFONATE

Using the procedure of Example 1A, phenyl vinylsulfonate is prepared from 253 g of phenol. Analysis: 14.8%–15.4% S.

EXAMPLE 2 — ADDUCTION OF O-CHLOROPHENYL VINYLSULFONATE TO POLYBUTENE 9.87 kg (10.39 g mols) of a polybutene having a number average molecular weight of 950 is charged, under nitrogen, to a reaction kettle. The polybutene is heated with stirring to 120° C. 2.73 kg (12.47 g mols) of o-chlorophenyl vinylsulfonate is added and the reaction mass is heated to 220° C with stirring and held at this temperature for 24 hours.

The reaction mass is then cooled to less than 65° C and 15 liters of methanol are added. The mass is refluxed at approximately 65° C for 45 minutes with stirring and still under nitrogen. After cooling to room temperature, phase separation takes place. If phase separation does not occur readily, another 4 to 8 liters of methanol can be added.

The bottom layer is withdrawn from the raction kettle and saved. The top layer is transferred to a storage tank. The bottom layer is returned to the kettle and another 15 liters of methanol are added to the kettle. The reaction mass is heated to reflux for 45 minutes with agitation, then cooled at room temperature and allowed to separate. The bottom layer is withdrawn from the kettle and the top layer is transferred to the storage vessel. The bottom layer is returned to the kettle and the container it was in is rinsed with 4 liters of hydrocarbon thinner which is added to the kettle. The riser to the condenser is heated to 82° C, but cold water is maintained on the heat exchanger. A vacuum is applied to the kettle and the contents are heated to 165° C maximum to distill off the thinner and methanol. The bottoms are cooled to room temperature and transferred to a storage container. Typical analysis: %S=1.46–1.54, %Cl=1.49–1.56.

EXAMPLE 3 — ADDUCT OF POLYISOBUTENYL CHLORIDE AND CHLOROPHENYL VINYLSULFONATE

Example 3A 512 g (0.357 mol) of a polyisobutenyl chloride (4%w chlorine) prepared from a polyisobutene having a number average molecular weight of 1400, and 94 g (0.43 mol) o-chlorophenyl vinylsulfonate are charged to a 1-liter flask. While maintaining a nitrogen atmosphere, the reaction mixture is heated with stirring at 210° C and maintained at that temperature for 7 hours. 16-ml samples are taken at 2, 4 and 7 hours for Hyamine titrations after conversion to the potassium salt. The Hyamine titration is used to determine the amount of anionic detergent in a sample. A known weight of sample is dissolved in chloroform and titrated with a dilute aqueous solution of Hyamine 1622. Acidic methylene blue is used as an indicator. The Hyamine solution is added in suitable increments with 2 minutes of vigorous shaking after each addition. The blue color is at first concentrated in the lower (chloroform) layer, but gradually appears in the upper (agueous) layer as the Hyamine is added. The end point is taken as that point at which the color in the two layers is equal. The millimols of sulfonate per gram of sample are equal to 25 VM/W, where V is the milliliters of Hyamine solution, M is the molarity of the Hyamine solution, and W is the grams of sample.

At the end of 7 hours, the remainder of the reaction mixture (532 g) is cooled and transferred to a 2-liter 3-neck flask equipped with a stirrer and a thermometer using 50 ml of a hydrocarbon thinner to flush the reaction flask. To the product/thinner mixture, 800 ml of methanol are added and the mixture is stirred at reflux (64° C) for 45 minutes. An emulsion is obtained which does not break on standing. An additional 200 ml of methanol and 200 ml of hydrocarbon thinner are added and the mixture is stirred for 2 minutes. The mixture is then allowed to settle at room temperature for 1.5 hours and the supernatant liquid (ca. 1100 ml) is decanted. 800 ml of methanol is added to the mixture remaining in the flask and stirred at reflux (63° C) for 45 minutes. Again, an emulsion is obtained. 200 ml of the hydrocarbon thinner is added and the mixture is stirred for 2 minutes. The mixture is then allowed to settle at room temperature for 1.5 hours and the supernatant liquid (ca. 1000 ml) is decanted. The extracted product remaining in the flask is dissolved in hydrocarbon thinner and transferred to a 1-liter, 3-neck flask with a small amount of solvent; the solvent is stripped off to an end point of 165° C at 5 mm Hg to yield 466 g of product. Analysis: S, 0.88%w; Cl, 1.19%w.

Example 3B 512 g (0.357mol) of a polyisobutenyl chloride (4%w chlorine prepared from a polyisobutene having a number average molecular weight of 1400), and 97 g (0.43 mol) o-chlorophenyl vinylsulfonate are charged to the flask. The reaction mixture is heated under nitrogen with stirring at 180° C for 10 hours. the off-gas is scrubbed through a sparger into an Erlenmeyer flask containing 200 ml water. 16-ml samples are withdrawn at 2, 4, 6 and 10 hours for Hyamine titration. The off-gas water trap is replaced each time a sample is taken. The water is titrated to a methyl orange end point with 3N-sodium hydroxide solution. The 4 titrations require 100, 32.3, 19 and 20.4 ml, respectively, for a total of 171.7 ml, which is equivalent to 0.515 mol of sodium hydroxide.

The remainder of the reaction mixture (530 g) is transferred to a 2-liter, 3-neck flask using about 50 ml of hydrocarbon thinner to rinse the reaction flask. 800 ml of methanol is added to the 3-neck flask and the mixture is refluxed with stirring for ¾ hour. Complete separation is not obtained when the stirring is stopped. 200 ml of n-hexane is added and the mixture is stirred for 2 minutes. After the mixture settles at room temperature for 1 hour, approximately 800 ml of supernatant liquid is decanted. 800 ml of methanol is added to the 2-liter flask and the mixture is refluxed for ¾ hour. After standing at room temperature for 1.5 hours, about 900 ml of supernatant liquid is decanted. The mixture remaining in the flask is dissolved in hydrocarbon thinner and transferred to a 1-liter, 3-neck flask. The solvent is stripped off the product to an end point of 165° C at 5 mm Hg to yield 460 g of product. Analysis: S, 0.99%w, Cl, 1.84%w.

Example 3C 506 g (0.5 mol) of polybutene chloride (4%w chlorine) prepared from a polyisobutene having a number average molecular weight of 950 is added to a 1 liter reaction flask under a nitrogen atmosphere. 142 g (0.65 nol) of o-chlorophenyl vinylsulfonate is then added. The reaction mass is heated under nitrogen with stirring at 210° C for 7 hours. 16-ml samples are withdrawn at 2, 4 and 7 hours for Hyamine titration. At the end of the 7-hour reaction period, the remainder of the reaction mixture (569 g) is transferred to a 2-liter, 3-neck flask using about 50 ml of the hydrocarbon thinner to rinse the reaction flask. 800 ml of methanol is added to the flask and the mixture is stirred at reflux (64° C) for about 45 minutes. The mixture is allowed to stand at room temperature for about 3½ hours. Fast separation is obtained, but only about 700 ml of supernatant liquid could be decanted. 800 ml of methanol is added and the mixture is stirred at reflux (64° C) for about 45 minutes. The mixture is allowed to stand at room temperature for 1¾ hours. Fast separation is again obtained, but only about 500 ml of supernatant liquid could be decanted. 600 ml of n-hexane is added to the flask and the mixture is stirred for 2 minutes. After settling for ¼ hour, about 550 ml of supernatant liquid is siphoned off. The mixture remaining in the flask is transferred to a 1-liter, 3-neck flask using a small amount of n-hexane to rinse the flask. The solvent is removed by stripping to 190° C at 5 mm Hg to yield 475 g of product. Analysis; S, 1.80%w; Cl 2.16%w.

Example 4
Preparation of Sodium Sulfonate

A 1-liter, 3-neck flask is charged with 210 g (ca. 0.1 mol) of o-chlorophenyl polyisobutenylethylsulfonate in which the polyisobutenyl group has a number average molecular weight of about 950. 200 ml of an inert hydrocarbon thinner are added and the sulfonate and the solvent are stirred to mix them. With stirring an aqueous solution of 11 g (0.27 mol) of sodium hydroxide in 15 ml of water is added and the reaction mass is heated at 120° C for 1.5 hours. The reaction mass is allowed to cool and to settle overnight and then is filtered through Hyflosupercel (diatomaceous earth).

The filtrate is transferred to a 2-liter separatory funnel, using 200 ml of the thinner as a rinse to insure complete transfer. 300 ml of 2-butanol and 300 ml of water are added and the contents of the funnel are mixed thoroughly. The contents of the funnel are allowed to settle for one-half hour and the bottom layer is drained off (ca. 260 ml). The nonaqueous phase remaining in the funnel is washed four times with approximately 600 ml of aqueous sodium chloride solution. The sodium chloride solution is used because water alone did not phase-separate well enough. The hydrocarbon phase is stripped of the butanol and any entrained water to an end point of 190° C at about 200 mm Hg.

The stripped product is cooled and 700 ml of hexane is added. The resulting mixture is filtered through Hyflosupercel. The filtrate is stripped free of solvent to 200° C at 5 mm Hg. 194 g of product having a slight haze are recovered. 80 g of a neutral solvent-refined lubricating oil having a viscosity of 100 SUS at 100° F (38° C) is added. This mixture is heated to 150° C with stirring to homogenize and then filtered through Hyflosupercel to yield a clear product. The product is analyzed with the following results: Na, 0.66%w; S, 0.96%w; Cl, 0.02%w.

Example 5 – Preparation of Calcium Sulfonate by Metathesis

To a 5-liter flask, 1060 g of o-chlorophenyl polyisobutenylethylsulfonate having a number average molecular weight of 950 and 1000 ml of an inert hydrocarbon thinner are added. Thereafter, 45 g of sodium hydroxide in 70 ml of water are added. With stirring the temperature is raised to 100° C and maintained there for 2 hours. After cooling to 95° C, a solution of 156 g of calcium chloride in 1000 ml of water is added. The reaction mass is stirred for 1 hour at 85° C.

The reaction mass is transferred to two four-liter separatory funnels and to each is added 750 ml of 2-butanol. The aqueous phase is drained off the bottom, the hydrocarbon phases are transferred to two five-liter, three-neck flasks and to each is added 80 g calcium chloride in 500 ml water. The mixtures are stirred for 1 hour at 85° C and then transferred to two separatory funnels as before. The aqueous phase is drained off the bottom and the hydrocarbon phase is washed again with a mixture of 80 g calcium chloride in 500 ml water and four times with water. The hydrocarbon phase is stripped free of solvent to 175° C at 5 mm Hg to yield 1018 g product. To the product is added 509 g of a neutral solvent-refined lubricating oil having a viscosity of 100 SUS at 100° F. The mixture is stirred at 150° C to homogenize it and is then filtered through Hyflosupercel, after which it was analyzed with the following results: Ca, 0.56%w; S, 0.84%w; Cl, 0.01%w.

Example 6 – Preparation of Calcium Sulfonate Directly

To a two-liter, three-neck flask are added 516 g (0.255 mol) of o-chlorophenyl polyisobutenylethylsulfonate in which the polyisobutenyl group has a number average molecular weight of 950 (1.58%w sulfur), 500 ml of an inert hydrocarbon hinner, 62 g (1 mol) of ethylene glycol, and 22 g (0.3 mol) of calcium hydroxide. The reaction mass is heated to 140°–145° C for 7.5 hours, diluted with 500 ml of a hydrocarbon thinner and filtered through Hyflosupercel. The thinner which was added just prior to filtration had a lower boiling point than that used during the reaction. The lower-boiling thinner was distilled off to a bottoms temperature of 105° C at 200 mm Hg to yield 839 g of solution having an AV equal to 23.

Example – Preparation of Calcium Sulfonate by Metathesis

To a five-liter, three-neck flask, equipped as in Example 4, is added 1350 g of phenyl polyisobutenylethylsulfonate, in which the polyisobutenyl group has a number average molecular weight of 950, dissolved in 2025 ml of an inert hydrocarbon solvent. A solution of 99 g (1.5 mols) of 85% potassium hydroxide dissolved in 300 ml of methanol is added. With stirring, the methanol is distilled off and the reaction mixture is maintained at 100° C for 2 hours. 800 ml of 2-butanol is added and the mixture is stirred at 79° C for 4 hours. The reaction mass is divided into two equal parts which are charged to five-liter, three-neck flasks, each of which is equipped with a stirrer, thermometer and reflux condenser. To each flask is added 400 ml of 2-butanol, 800 ml of water, and 500 ml of the inert hydrocarbon solvent. The reaction masses are stirred at 80° C for one-half hour and then transferred to separatory funnels where they are allowed to settle and the water layers are drawn off. Each of the remaining hydrocarbon phases is transferred to separate five-liter, three-neck flasks equipped as above. Each is stirred three times with a solution of 147 g of calcium chloride dihydrate in 800 ml of water for one hour at 80° C and is then water-washed three times with 800 ml of water for 0.75 hour at 80° C. After the last water wash has been separated from the hydrocarbon layer, the supernatant liquid is filtered through Hyflosupercel. The filtrate is stripped free of the hydrocarbon solvent to 170° C bottoms temperature of 5 mm Hg to yield 1142 g of combined product. The quantity of product was low because some product was lost during the workup. 613 g of a neutral solvent-refined lubricating oil having a viscosity of 100 SUS at 100° F is added to the product to yield 1755 g of concentrate. The concentrate had a slight haze, which was removed by filtering through Hyflosupercel. The concentrate is analyzed and found to contain: Ca, 0.65%w; S, 1.07%w; Cl, less than 0.01%w.

Example 8

A one-liter, three-neck flask equipped with a stirrer, thermometer, and gas inlet, is charged with 200 g calcium polyisobutenylethylsulfonate in which the polyisobutenyl group has a number average molecular weight of 1400, 500 ml xylene, 50 ml methanol, 67 ml 2-ethylhexanol, and 60 g calcium hydroxide. The mixture is carbonated with 28 g of carbon dioxide at room temperature (25°–49° C) over a period of 45 minutes. The introduction of carbon dioxide is discontinued when the appearance of offgas is observed.

The temperature of the reaction mixture is increased to 135° C to distill off the methanol and water. The mixture is then cooled, is filtered through Hyflosupercel, and is stripped free of solvent to 175° C at 5 mm Hg. After a final filtration through Hyflosupercel, the product contains 8.88% calcium and has a base ratio of 18.7 and AV of 236.

Example 9
1-G Caterpillar test

The lubricating oil compositions of this invention are tested in the well-known 1-G Caterpillar test. In this test, a single-cylinder diesel engine having a 5⅛ inch bore by 6½ inch stroke is operated under the following conditions; timing, °BTDC 8; brake mean effective pressure, PSI 141; brake horsepower 42; BTU's per minute 5850; speed 1800 rpm; air boost, 53 inches Hg absolute; air temperature in, 255° F (124° C); water temperature out, 190° F (88° C); and sulfur in fuel, 0.4%w. At the end of each 12 hours of operation, sufficient oil is drained from the crankcase to allow addition of one quart of oil. In the test on the lubricating oil compositions of this invention, the 1-G test is run for the hours shown in Table I. At the end of this period, the engine is dismantled and rated for cleanliness. The ring lands are rated on a scale of 0 to 800, with 0 representing clean and 800 representing black deposits. The ring grooves are rated on a scale of 0% to 100% groove fill, with 0 representing clean. The underhead of the piston is rated on a scale of 0 to 10, with 0 representing dirty and 10 representing clean.

The base oil used in these tests is a mid-continent base stock SAE 30 oil containing a conventional succinimide dispersant, a calcium phenate, and a zinc dithiophosphate. To this base oil is added 10 mmols of the calcium sulfonate to be tested. For comparison, commercially available calcium sulfonates are tested. The sulfonate designed as A in Table I below is a commercially available calcium sulfonate prepared by acid-treating a neutral solvent-refined lubricating oil having a viscosity of between 300 and 480 SUS. The sulfonate designated at B in Table I is a commercially available mixture of calcium sulfonates derived from various sources such as acid-treated neutral solvent-refined lubricating oils as well as certain of the hard alkylates produced as by-products in detergent manufacture. The results of testing the lubricating oils of this invention as well as lubricating oils containing the commercially available sulfonates are set forth in Table I.

TABLE I

| | | 120 Hr 1-G Caterpillar Test | | |
|---|---|---|---|---|
| Sulfonate | Hours | Grooves | Lands | Underhead |
| A | 60 | 58-4-0.6-0.5 | 160-310-215 | 4.8 |
| B | 60 | 50-6-0.6-0.7 | 390-120-515 | 4.8 |
| Ex. 5 | 60 | 22-4-1.0-0.9 | 105-20-25 | 6.6 |
| Ex. 7 | 60 | 27-8-1.0-0.6 | 165-30-25 | 5.7 |
| | 120 | 38-7-2-0.6 | 168-39-48 | 4.5 |

From the data in Table I, it can be seen that the calcium sulfonates of this invention are good detergents in lubricating oil compositions. It should be noted that the lubricating oil compositions of this invention provide a significant improvement in the rating of the lower lands of the pistons compared to the lubricating oils containing the commercially available sulfonate detergents.

What is claimed is:

1. An oil-soluble Group I or Group II metal or lead salt of a substantially saturated aliphatic hydrocarbylethylsulfonic acid in which the substantially saturated aliphatic hydrocarbyl group contains from about 50 to about 200 carbons atoms.

2. A salt of claim 1 wherein the Group I metal is lithium, potassium or sodium and the Group II metal is magnesium, calcium, strontium, barium or zinc.

3. A salt of claim 2 wherein the Group I metal is sodium or potassium and the Group II metal is magnesium, calcium or barium.

4. A Group I or Group II metal salt of claim 1 wherein the hydrocarbyl group is polyisobutenyl.

5. A salt of claim 4 wherein the metal is magnesium, calcium, strontium, barium or zinc.

6. A salt of claim 4 wherein the polyisobutenyl group contains from 50–200 carbon atoms.

7. A salt of claim 4 wherein the Group I metal is sodium or potassium and the Group II metal is magnesium, calcium or barium.

8. An oil-soluble Group I or Group II metal or lead salt of a sulfonic acid of the formula:

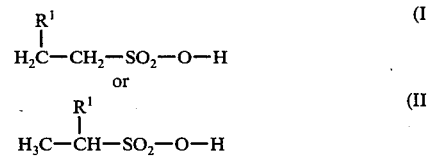

wherein $R^1$ is a substantially saturated aliphatic hydrocarbyl group containing about 50–200 carbon atoms and 0–3 sites of olefinic unsaturation.

9. A salt of claim 8 wherein the Group I metal is lithium, potassium or sodium and the Group II metal is magnesium, calcium, strontium, barium or zinc.

10. A salt of claim 9 wherein $R^1$ is a substantially saturated aliphatic hydrocarbyl containing 0–2 sites of olefinic unsaturation.

11. A salt of claim 10 wherein the Group I metal is sodium or potassium, the Group II metal is magnesium, calcium or barium, and $R^1$ is polyisobutenyl.

12. A process for preparing an oil-soluble Group I or Group II metal salt of a substantially saturated aliphatic hydrocarbyl ethylsulfonic acid, in which the substantially saturated aliphatic hydrocarbyl substituent contains at least 25 aliphatic carbon atoms, comprising reacting an aryl ester of the substantially saturated aliphatic hydrocarbyl ethylsulfonic acid with a Group I or Group II metal oxide or hydroxide thereby forming said Group I or Group II metal salt.

13. A process of claim 12 wherein the Group I metal is lithium, potassium or sodium, the Group II metal is magnesium, calcium, strontium, barium or zinc, and the Group I or Group II metal compound is a Group I or Group II metal hydroxide.

14. A process of claim 13 wherein the hydrocarbyl group contains from about 25 to about 350 aliphatic carbon atoms.

15. The process of claim 14 wherein the Group I metal is sodium or potassium, the Group II metal is magnesium, calcium or barium, and the hydrocarbyl group is polyisobutenyl.

16. A process for preparing an oil-soluble Group I or Group II metal salt of a sulfonic acid of the formula:

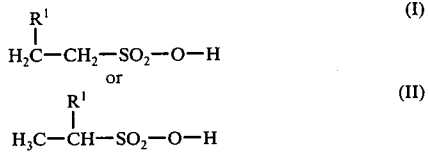

wherein $R^1$ represents a substantially saturated aliphatic hydrocarbyl containing about 25–350 aliphatic carbon atoms and 0–3 sites of olefinic unsaturation, comprising reacting an aryl ester of a substantially saturated hydrocarbyl ethylsulfonic acid with a Group I or Group II metal oxide or hydroxide thereby forming said Group I or Group II metal salt.

17. The process of claim 16 wherein the Group I metal is lithium, potassium, or sodium, the Group II metal is magnesium, calcium, strontium, barium or zinc, Group I or Group II metal compound is a Group I or Group II metal hydroxide, and $R^1$ is a substantially saturated hydrocarbyl group containing 50–200 carbon atoms and 0–2 sites of olefinic unsaturation.

18. A process for preparing an oil-soluble Group II metal or lead salt of a substantially saturated aliphatic hydrocarbylethylsulfonic acid, in which the substantially saturated hydrocarbyl contains at least 25 aliphatic carbon atoms, comprising:
 1. contacting an aryl ester of the substantially saturated hydrocarbylethylsulfonic acid with a Group I metal oxide or hydroxide to form a first reaction product, and
 2. contacting the first reaction product with a water-soluble Group II metal or lead salt to form the Group II metal or lead salt of the substantially saturated hydrocarbylethylsulfonic acid.

19. The process of claim 18 wherein the Group I metal hydroxide is sodium hydroxide or potassium hydroxide, the Group II metal salt is magnesium chloride, calcium chloride, strontium chloride, barium chloride, or zinc chloride, and the hydrocarbyl group contains from about 25 to about 350 aliphatic carbon atoms.

20. The process of claim 19 wherein the Group II metal salt is magnesium chloride, calcium chloride, or barium chloride, and the hydrocarbyl group contains from about 50 to about 200 aliphatic carbon atoms.

21. A concentrated lubricating oil additive composition comprising:

(a) 85%–15% weight of an oil of lubricating viscosity, and
(b) 15%–85% weight of an oil-soluble Group I or Group II metal or lead salt of a substantially saturated aliphatic hydrocarbylethylsulfonic acid in which the substantially saturated hydrocarbyl group contains 50–200 aliphatic carbon atoms.

22. A concentrated lubricating oil additive composition of claim 21 wherein the Group I or Group II metal salt is a lithium, potassium, sodium, magnesium, calcium, barium, strontium, or zinc salt and the hydrocarbyl group contains from about 50 to about 200 carbon atoms.

23. A concentrated lubricating oil additive composition of claim 22 comprising:
(a) 85%–15% weight of the oil of lubricating viscosity, and
(b) 15%–85% weight of the oil-soluble salt wherein the metal is calcium, barium, magnesium, strontium or zinc and the hydrocarbyl group contains from 50 to 200 carbon atoms.

24. A concentrated lubricating oil additive composition of claim 23 wherein the Group II metal salt is a calcium, barium or magnesium salt of polyisobutenylethylsulfonic acid.

25. A composition comprising:
 a major amount of an oil of lubricating viscosity, and
 a detergent-dispersant amount up to 15% by weight of an oil-soluble Group I or Group II metal or lead salt of a substantially saturated aliphatic hydrocarbyl ethylsulfonic acid in which the substantially saturated hydrocarbyl group contains 50–200 carbon atoms.

26. A composition of claim 25 wherein the salt is a Group II salt.

27. A composition of claim 26 wherein the Group II salt is calcium, barium or magnesium.

28. A composition of claim 27 wherein the hydrocarbyl group is polyisobutenyl.

29. A composition of claim 25 containing from 0.1% up to 10% weight of the oil-soluble salt.

30. An oil-soluble Group II metal carbonate overbased Group I or Group II metal or lead salt of a sulfonic acid of the formula:

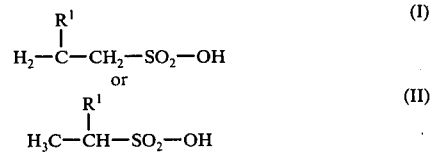

wherein $R^1$ is a substantially saturated aliphatic hydrocarbyl group containing about 50–200 carbon atoms and 0–3 sites of olefinic unsaturation.

31. A salt of claim 30 wherein the Group II metal is magnesium, calcium or barium, the Group I metal is sodium or potassium, $R^1$ is polyisobutenyl of 50–200 carbon atoms and the alkalinity value is from 0.1 to about 400.

32. A lubricating oil concentrate containing 15%–85% by weight of an oil of lubricating viscosity and 85%–15% by weight of a salt of claim 30.

33. A lubricating oil containing a major amount of an oil of lubricating viscosity and a minor amount up to 15% of salt of claim 31.

34. The product prepared by the process of claim 16.

35. A lubricating oil containing an oil of lubricating viscosity and a detergent amount of the salt of claim 34.

* * * * *